(12) United States Patent
Lane et al.

(10) Patent No.: US 7,226,419 B2
(45) Date of Patent: Jun. 5, 2007

(54) MODE DETECTION AND SAFETY MONITORING IN BLOOD PRESSURE MEASUREMENT

(75) Inventors: John A. Lane, Weedsport, NY (US); David E. Quinn, Auburn, NY (US); Craig M. Meyerson, Syracuse, NY (US); Tyson B. Whitaker, Arden, NC (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 14 days.

(21) Appl. No.: 11/158,773

(22) Filed: Jun. 22, 2005

(65) Prior Publication Data

US 2006/0293601 A1   Dec. 28, 2006

(51) Int. Cl.
*A61B 5/02* (2006.01)

(52) U.S. Cl. .................. 600/490; 600/494; 600/496

(58) Field of Classification Search ............... None
See application file for complete search history.

(56) References Cited

U.S. PATENT DOCUMENTS

| | | | |
|---|---|---|---|
| 4,216,779 A | 8/1980 | Squires et al. | |
| 4,501,280 A | 2/1985 | Hood, Jr. | |
| 4,572,205 A | 2/1986 | Sjonell | |
| 4,768,518 A | 9/1988 | Peltonen | |
| 4,924,873 A | 5/1990 | Sorensen | |
| 4,953,557 A * | 9/1990 | Frankenreiter et al. | 600/493 |
| 5,003,981 A | 4/1991 | Kankkunen et al. | |
| 5,022,403 A | 6/1991 | LaViola | |
| 5,060,654 A | 10/1991 | Malkamaki et al. | |
| 5,240,008 A | 8/1993 | Newell | |
| 5,301,676 A | 4/1994 | Rantala et al. | |
| 5,447,160 A | 9/1995 | Kankkunen et al. | |
| 6,171,254 B1 | 1/2001 | Skelton | |
| 6,450,966 B1 | 9/2002 | Hanna | |
| 2003/0093001 A1 | 5/2003 | Martikainen | |

* cited by examiner

*Primary Examiner*—Robert L. Nasser
(74) *Attorney, Agent, or Firm*—Marjama & Bilinski LLP (57) ABSTRACT

A method is provided for blood pressure measurement by means of an inflatable cuff (50) applied to a limb of a vertebrate and pneumatically coupled to a first port (112A) and a second port (112B) of a blood pressure measurement apparatus (100). A pump (160) coupled to the second port inflates the cuff pneumatically. During an initial cuff inflation period, a first pressure sensor (180) pneumatically coupled to the first port senses a first pressure and a second pressure sensor (182) pneumatically coupled to the second port senses a second pressure. An analysis module (142) compares the magnitude of the first pressure to the magnitude of the second pressure to determine the relative relationship between the respective magnitudes of the first pressure and the second pressure. The relative relationship between these pressure may be used to determine whether a single lumen or dual lumen cuff is use, to determine whether the blood pressure measurement procedure selected is correct for the cuff actually in use, or to automatically select the proper blood pressure measurement procedure to be used for the actual cuff in use.

21 Claims, 8 Drawing Sheets

MODE DETECTION AND SAFETY MONITORING IN BLOOD PRESSURE MEASUREMENT

CROSS-REFERENCE TO RELATED APPLICATIONS

This application is related to co-pending U.S. patent application Ser. No. 10/619,380, filed Jul. 14, 2003, entitled "Motion Management in a Blood Pressure Measurement Device," published Feb. 10, 2005, as Patent Application Publication No. US2005/0033188A1, and subject to assignment to the common assignee of the present application, which application is incorporated herein by reference in its entirety. This application is also related to co-pending U.S. patent application Ser. No. 11/032,625, filed Jan. 10, 2005, entitled "A Portable Vital Signs Measurement Instrument and Method of Use Thereof," and subject to assignment to the common assignee of the present application, which application is incorporated herein by reference in its entirety.

FIELD OF THE INVENTION

The present relates generally to blood pressure monitoring devices and, more particularly, to a method for the identification of the cuff type connected to a blood pressure monitor at the initiation of a measurement procedure to ensure that the correct cuff type and the correct measurement mode are in use for the patient.

BACKGROUND OF THE INVENTION

The measurement of blood pressure is a common procedure used in hospitals, clinics and physicians' offices as a tool to assist in diagnosis of illness and monitoring of sick patients, as well as an indicator of the general status of a person's health. In standard non-invasive blood pressure measurement practice, blood pressure is measured using an inflatable cuff that is wrapped about a patient's arm or leg. The cuff is then inflated to provide a certain amount of pressure on the artery in the arm or leg beneath the cuff. The cuff is inflated by air supplied by means of an inflation device, such as a pneumatic bulb or an electric pump, connected to the cuff by a tube or tubes. The systolic and diastolic blood pressures are determined as the air inflating the cuff is slowly released thereby deflating the cuff and reducing the pressure on the artery.

The initial pressure to which the cuff is inflated depends upon the particular patient whose blood pressure is being measured. The pressure to which the cuff is initially inflated will be higher for an adult, than for a child, than for an infant, than for a neonate. The maximum pressure to which the cuff is inflated must be controlled to ensure that the patient is not injured by the pressure. This is particularly necessary when measuring the blood pressure of a neonate. Additionally, as the size of the limbs of an adult male will be greater than the size of the limbs of a child or a neonate, different size cuffs are available. For example, cuffs are available sized for use on large adults, average adults, small adults, children, small children, infants and neonates.

Electronic blood pressure measurement devices are in common use that automatically performs a blood pressure measurement procedure, either upon initiation by a clinician or at selected preprogrammed intervals. In using such automatic measurement devices, the clinician must select the mode of measurement to be used, e.g. adult, pediatric, infant, or neonatal. The clinician must also remember to connect the correct blood pressure cuff to the device before initiating a measurement procedure. Therefore, the potential exists for an incorrect cuff to be inadvertently connected to an automatic blood pressure measurement device that is an improper cuff type may be connected with respect to the patient whose blood pressure is to be measured.

Automatic sphygmomanometers are known that are programmed to identify the particular cuff connected to the sphygmomanometer. For example, in U.S. Pat. No. 6,171,254, Skelton discloses an automatic blood pressure monitor for unattended operation wherein the pressure-time characteristic is monitored during initial pressurization of the cuff to determine the cuff size in use. The cuff size in use is determined by matching the initial pressure-time characteristic measured against a set of predetermined pressure-time characteristics for known cuff sizes that are stored in a microprocessor associated with the automatic blood pressure monitor. Having determined the cuff size in use, the microprocessor controls the inflation process to pressurize the cuff to a preselected pressure for that cuff size and deflates the cuff in accord with a preselected deflation sequence for the particular size cuff in use.

U.S. Pat. No. 4,501,280, Hood, Jr., discloses an automated blood pressure monitor adapted to use a variety of cuff sizes, including neonatal, wherein the time of propagation of an acoustical pressure pulse through the cuff and back to a pressure transducer in the monitor is used to verify the type of cuff in use in connection with the monitor. Prior to execution of a blood pressure measurement routine, the cuff is inflated to a given pressure, whereupon a pressure control valve is opened thereby creating a pressure/acoustical pulse which propagates at the speed of sound through the cuff and back to the pressure transducer in the monitor. The total time of propagation is measured and compared to a predetermined threshold intermediate the typical propagation times of neonatal and adult cuffs, respectfully.

U.S. Pat. No. 5,060,654, Malkamaki et al., discloses an automatic identification method for the cuff of a sphygmomanometer wherein a pressure pulse is trigger from a valve upstream of the cuff to a pressure sensing element downstream of the cuff. The pulse width is measured and compared with a predetermined pulse width threshold value to distinguish between a smaller cuff and a larger cuff.

U.S. Pat. No. 5,003,981, Kankkunen et al., discloses a method for identification of the cuff being used in connection with a non-invasive automatic sphygmomanometer wherein a flow restriction means, such as an orifice, is disposed in the tube from the pump to the cuff. To identify the cuff in use, the cuff is rapidly inflated to a pressure of 20–30 mmHg. The inflation is abruptly stopped and the change in the pressure differential across the flow restriction means is monitored as the pressure downstream and upstream of the flow restriction means equalizes. A control element identifies the size of the cuff on the basis of data received from the sensor.

U.S. Pat. No. 6,450,966, Hanna, also discloses a method for automatically identifying a given cuff out of a plurality of cuffs wherein a different flow restrictor is associated with each cuff type. Prior to a blood pressure measurement procedure, the cuff is at least partially and then deflated through the flow restrictor. A pressure measurement is taken downstream of the flow restrictor during the deflation process and this pressure measurement is used to identify the particular type of cuff in use.

U.S. Pat. No. 5,301,676, Rantala et al., also discloses a method for automatically identifying a given cuff of at least a pair of cuffs wherein a flow restrictor is associated with at least one of the cuffs. Prior to a blood pressure measurement procedure, the cuff is inflated and the pressure magnitude variations sensed both upstream and downstream of the cuff. The sensed upstream and downstream pressure magnitude variations are compared and from this comparison which cuff is connected to the sphygmomanometer is determined.

Although the aforementioned methods of automatically identifying what cuff is connected to an automatic sphygmomanometer are effective, some of these methods require a distinct cuff identification procedure prior to initiation of a blood pressure measurement routine. Some of these methods require that a sensed pressure characteristic associated with the cuff in use be compared to a set of predetermined pressure related characteristics for a respective set of cuffs be preprogrammed into the sphygmomanometer memory for identification of the cuff in use. As such, the method may only be used to identify cuffs for which the required pressure characteristic has been preprogrammed.

SUMMARY OF THE INVENTION

It is an object of the present invention to provide a method for ensuring that automated blood pressure measurement of a neonate may only proceed if a suitable cuff is used and the proper blood pressure measurement procedure is employed.

It is an object of a further aspect of the present invention to provide of method for identifying the mode selected in real time during the initial stage of pressurizing the cuff during a blood pressure measurement procedure with no additional process time required.

In one aspect, the invention provides a method for blood pressure measurement by means of an inflatable cuff applied to a limb of a vertebrate and pneumatically coupled to a first port and a second port of a blood pressure measurement apparatus having a pump for inflating the cuff pneumatically coupled to the second port. The method comprises the steps of initiating inflation of the inflatable cuff, sensing a first pressure through a first pressure sensor pneumatically coupled to the first port, sensing a second pressure through a second pressure sensor pneumatically coupled to the second port, and comparing the magnitude of the pressure sensed by the first pressure sensor to the magnitude of the pressure sensed by the second pressure. If the magnitude of the pressure sensed by the first pressure sensor and the magnitude of the pressure sensed by the second pressure sensor are approximately equal, then the cuff configuration is identified as single lumen cuff. If the magnitude of the pressure sensed by the second pressure sensor exceeds the magnitude of the pressure sensed by the first pressure sensor, then the cuff configuration is identified as dual lumen cuff.

The method of the invention may be used in connection with a blood pressure measurement apparatus wherein the user may select a blood pressure measurement procedure to be implemented from a set of options including a first blood pressure measurement procedure which requires a dual lumen cuff configuration and a second blood pressure measurement procedure which requires a single lumen cuff configuration. After the user selects the desired mode, inflation of the cuff is initiated and the magnitude of the pressure sensed by the first pressure sensor is compared to the magnitude of the pressure sensed by the second pressure sensor. If the comparison matches the pressure relationship characteristic of the selected blood pressure measurement procedure, cuff inflation is continued. However, if the comparison does not match the pressure relationship characteristic of the selected blood pressure measurement procedure, cuff inflation may be promptly discontinued and the blood pressure measurement procedure aborted or a switch could be made automatically in real time to a blood pressure measurement procedure having a pressure relationship characteristic matching the sensed pressure relationship with no additional process time.

The method of the invention may be used in connection with a blood pressure measurement apparatus capable of implementing both a first blood pressure measurement procedure which requires a dual lumen cuff configuration and a second blood pressure measurement procedure which requires a single lumen cuff configuration, without the user selecting the desired mode. Inflation of the cuff is initiated and the magnitude of the pressure sensed by the first pressure sensor is compared to the magnitude of the pressure sensed by the second pressure sensor. If the comparison matches the pressure relationship characteristic of a dual lumen cuff configuration, the controller selects the first blood pressure measurement procedure and the blood pressure measurement process continues. If the comparison matches the pressure relationship characteristic of a single lumen cuff configuration, the controller selects the second blood pressure measurement procedure and the blood pressure measurement process continues. The selection is made automatically in real time without additional process time required.

The method of the invention may be used in connection with a blood pressure measurement apparatus wherein the user selects a non-neonate blood pressure measurement procedure to be implemented from a set of options including a non-neonate blood pressure measurement procedure which requires a dual lumen cuff configuration and a neonate blood pressure measurement procedure which requires a single lumen cuff configuration. With the non-neonate mode selected, inflation of the cuff is initiated and the magnitude of the pressure sensed by the first pressure sensor is compared to the magnitude of the pressure sensed by the second pressure sensor. If the magnitude of the pressure sensed by the second pressure significantly exceeds the magnitude of the pressure sensed by the first pressure, thereby indicating a dual lumen cuff configuration in use, inflation of the cuff continues and blood pressure is measured via the selected non-neonate procedure. However, if the magnitude of the pressure measured by the second pressure sensor does not significantly exceed the magnitude of the pressure measured by the first pressure sensor, thereby indicating that a single lumen cuff configuration is in use, initiation of the cuff is terminated and the blood pressure measurement aborted. Alternatively, rather than aborting the process, if desired, a switch could be made automatically in real time to the neonate blood pressure measurement procedure with no additional process time.

The method of the invention may be used in connection with a blood pressure measurement apparatus wherein the user selects a neonate blood pressure measurement procedure to be implemented from a set of options including a non-neonate blood pressure measurement procedure which requires a dual lumen cuff configuration and a neonate blood pressure measurement procedure which requires a single lumen cuff configuration. With the neonate mode selected, inflation of the cuff is initiated and the magnitude of the pressure sensed by the first pressure sensor is compared to the magnitude of the pressure sensed by the second pressure sensor. If the magnitude of the pressure sensed by the second pressure sensor does not significantly exceed the magnitude of the pressure sensed by the first pressure sensor, thereby indicating that a single lumen cuff configuration is in use, inflation of the cuff continues and blood pressure is measured via the selected non-neonate procedure. However, if the magnitude of the pressure measured by the second pressure sensor does significantly exceed the magnitude of the pressure measured by the first pressure sensor, thereby indicating that a dual lumen cuff configuration is in use, initiation of the cuff is terminated and the blood pressure measurement aborted. Alternatively, rather than aborting the process, if desired, a switch could be made automatically in real time to the non-neonate blood pressure measurement procedure with no additional process time.

Accordingly, through use of the method of the present invention, the neonatal population can be protected against the mistaken application of a non-neonatal blood pressure measurement procedure as the method of the invention can distinguish between a neonatal procedure associated with a single lumen cuff configuration and non-neonatal procedure associated with a dual lumen cuff configuration. The method of the invention can also distinguish one neonatal blood pressure measurement procedure associated with a single lumen cuff configuration from another neonatal blood pressure measurement procedure associated with a dual lumen cuff configuration. The method of the invention can also distinguish one non-neonatal blood pressure measurement procedure associated with a single lumen cuff configuration from another non-neonatal blood pressure measurement procedure associated with a dual lumen cuff configuration.

In another aspect, the invention provides a blood pressure measurement apparatus for use in connection with an inflatable cuff applied to a limb of a vertebrate and pneumatically coupled to the apparatus by at least one lumen. The apparatus includes a pump selectively operable to inflate the inflatable cuff during an inflation period and having an outlet pneumatically coupled to at least one lumen, a first pressure sensor operatively associated with the at least one lumen for sensing the pressure in the cuff during an inflation period, a second pressure sensor operatively associated with the pump for sensing the pressure in the at least one lumen near the outlet of the pump, and an analysis module operatively associated with the first pressure sensor for receiving a first sensed pressure signal therefrom and the second pressure sensor for receiving a second sensed pressure signal therefrom. The analysis module configured to compare the first sensed pressure to the second sensed pressure signal during the inflation period and to generate a first comparison signal if the first and second sensed pressure signals are not approximately equal to each other and to generate a second comparison signal if the first and second sensed pressure signals are approximately equal to each other. The apparatus may further include a control module operatively associated with the pump and the analysis module, the control module configured to control the operation of the pump in response to receipt of one of either the first comparison signal or the second comparison signal from the analysis module. The apparatus may also include a user interface operatively associated with the control module, the user interface providing for a user of the apparatus to select one of either a first blood pressure measurement procedure or a second blood pressure measurement procedure to be conducted by the control module.

In one aspect, control module may be configured to terminate inflation of the cuff by the pump in accord with the first blood pressure measurement procedure in the event that the control module receives the second comparison signal from the analysis module.

In one aspect, the control module may be configured to continue inflation of the cuff by the pump in accord with the first blood pressure measurement procedure so long as the control module receives the first comparison signal from the analysis module.

In a further aspect, the control module may be configured to terminate inflation of the cuff by the pump in accord with the second blood pressure measurement procedure in the event that the control module receives the first comparison signal from the analysis module.

In a further aspect, the control module may be configured to continue inflation of the cuff by the pump in accord with the second blood pressure measurement procedure so long as the control module receives the second comparison signal from the analysis module.

Advantageously, the first blood pressure measurement procedure may be for measurement of the blood pressure on non-neonate vertebrates only, and the second blood pressure measurement procedure may be for measurement of the blood pressure on neonate vertebrates only.

In one aspect, the invention provides a for use in connection with an inflatable cuff applied to a limb of a non-neonate vertebrate and pneumatically coupled to the apparatus through a single lumen. The apparatus comprises a first pressure sensor pneumatically coupled with the lumen through a first port of the apparatus and operative to sense the pressure at the first port during a period of inflation of the cuff, a second pressure sensor pneumatically coupled with the lumen through a second port of the apparatus and operative to sense the pressure at the second port during a period of inflation of the cuff, and a shunt providing a conduit pneumatically coupling the first port and the second port of the apparatus to the single lumen. The shunt may have a first port being connected to the first port of the apparatus, a second port being connected to the second port of the apparatus, and a third port being connected to the distal end of the lumen. Advantageously, the may be formed integrally with a distal end of the lumen.

DETAILED DESCRIPTION OF THE INVENTION

Figure 1A:
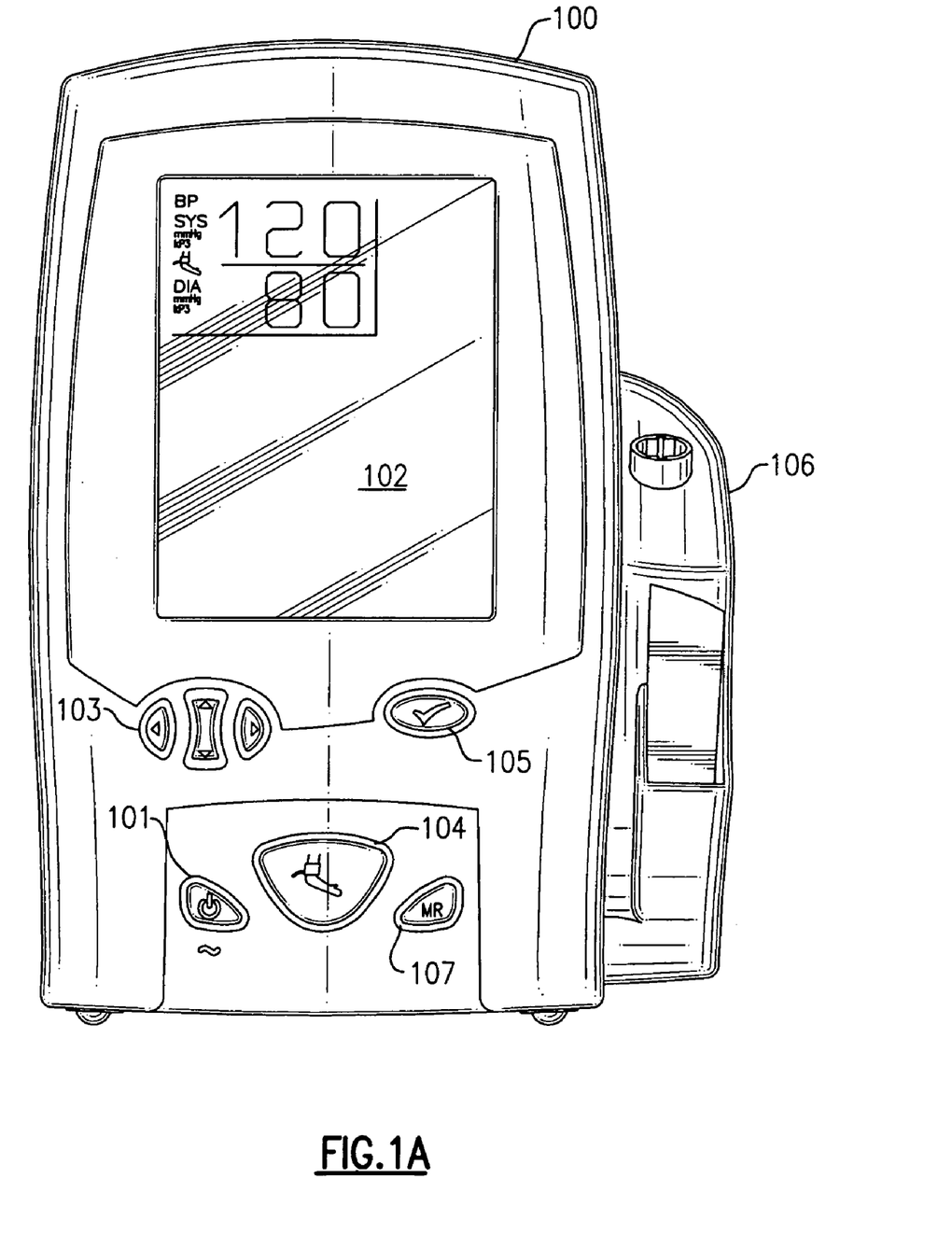
FIG. 1A is a front elevation view of an exemplary embodiment of a vital signs measurement apparatus for non-invasive blood pressure measurement.
Figure 1B:
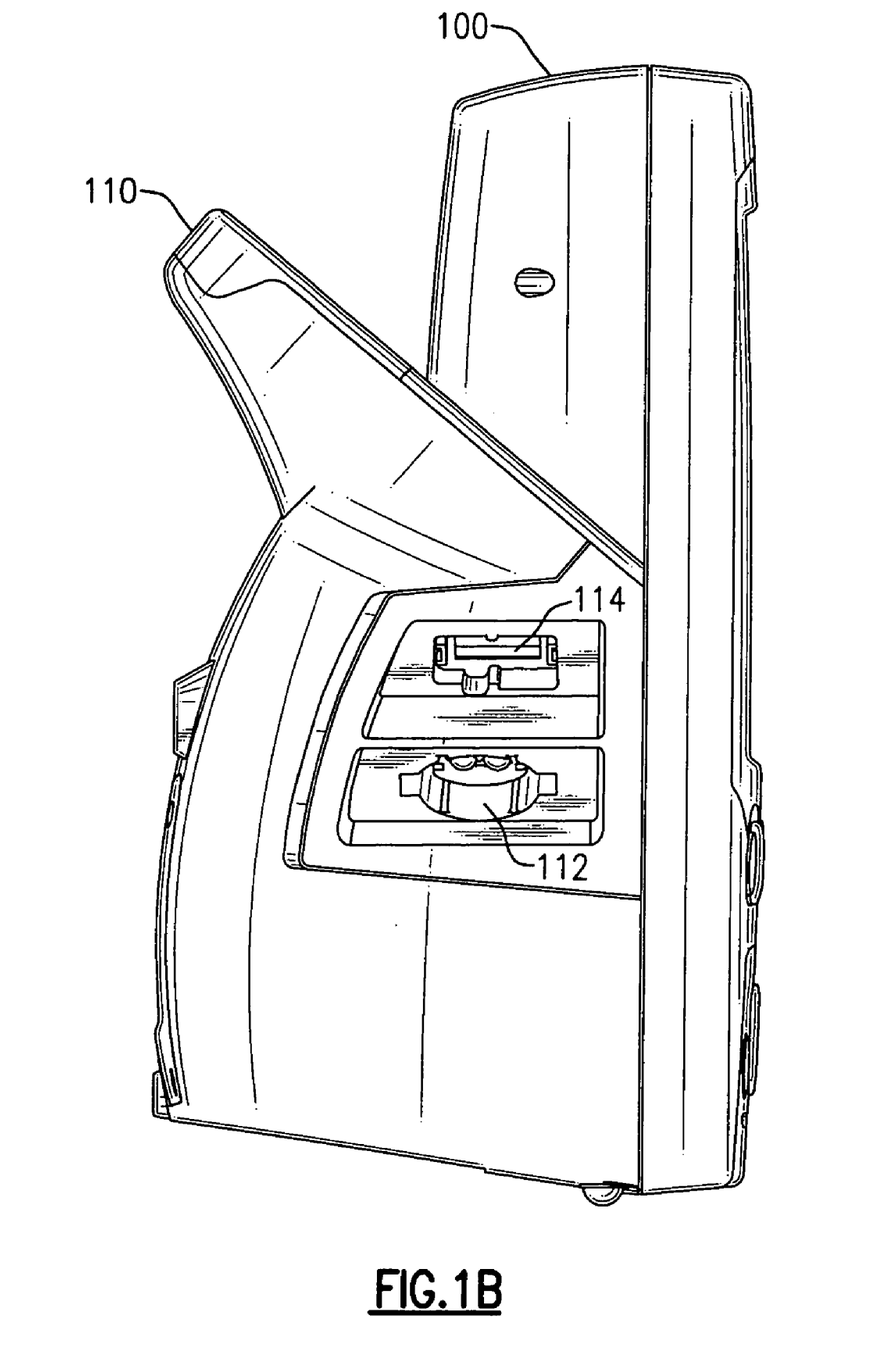
FIG. 1B is an elevation view of the left side of the vital signs measurement apparatus depicted in FIG. 1A.
Figure 1C:
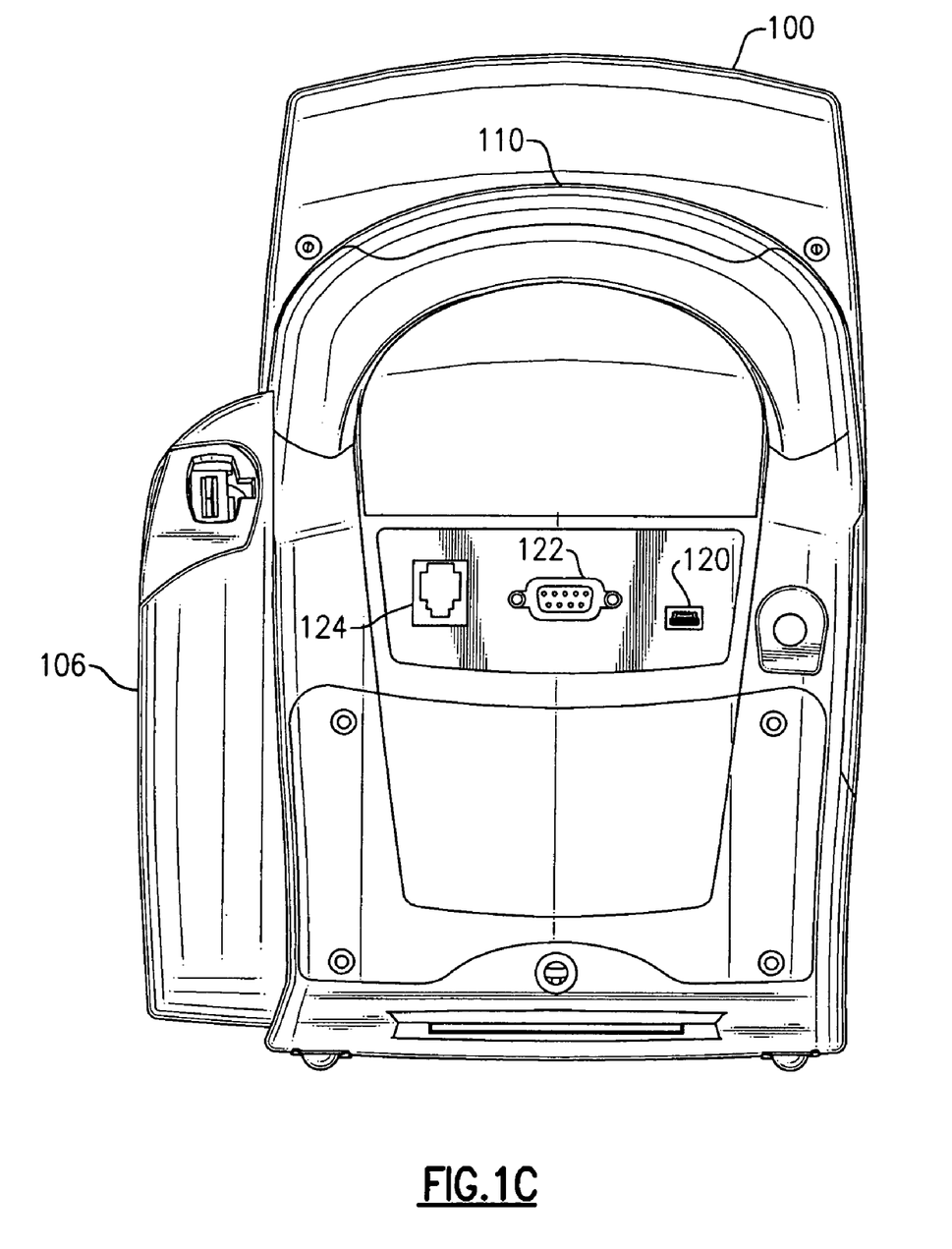
FIG. 1C is an elevation view of the back of the vital signs measurement apparatus depicted in FIG. 1A.

The present invention will be described herein with reference to an exemplary embodiment of a portable vital signs measurement apparatus 100 depicted in FIGS. 1A through 1C. It is to be understood, however, that the exemplary embodiment the portable vital signs measurement apparatus depicted in FIGS. 1A through 1C is illustrative and not limiting of the present invention. Those skilled in the art will recognize that the present invention may be applied to other embodiments of blood pressure monitoring devices.

Referring now to the drawings, and FIGS. 1A through 1C in particular, there is depicted therein a portable vital signs measurement apparatus including a connector 112 for connection to a blood pressure cuff for measuring at least one of the diastolic and systolic blood pressures of a patient wearing the blood pressure cuff connected to connector 112. In the exemplary embodiment depicted in FIGS. 1A through 1B, the vital signs measurement apparatus 100 a display 102, a plurality of keys 101, 103, 104, 105 and 107, and a handle 110. The handle 110 provides portability, thereby enabling a clinician to move the vital signs measurement apparatus 100 from room to room in a patient care facility, to sit the apparatus 100 on a table or stand close to a patient, or to place the apparatus 100 on a mobile stand that may be wheeled about.

The display 102 includes a region for displaying information relating to a blood pressure measurement including the systolic blood pressure (SYS) and the diastolic blood pressure (DIA) measurements in either milligrams of Mercury ("mmHg") or pascals ("kPa"). Both the systolic and diastolic blood pressures are displayed as a numeric three digit number. For purposes of illustration, the systolic and diastolic blood pressures are shown in FIG. 1 as 120 mmHg and 80 mmHg, respectively.

Key 101 is an on/off switch for selectively powering the apparatus 100 on and off. Key 103 is a four way directional switch for navigating through options displayed on the display 102. Key 105 is a select button for selecting options and responding to prompts on the display 102. Key 107 is a memory recall button for selectively recalling stored patient data sets for display on the display 102. Key 104 is a start/stop switch for selectively starting and then stopping a blood pressure measurement cycle.

To facilitate transfer of data to and communications with external devices, the vital signs measurement apparatus 100 may include a USB port 120, an RS232 port 122 and a 9 wire serial connector port 124, as depicted in FIG. 1C. However, in other embodiments, different types of connectors can be used as one or both of connectors 122 and 124, such as an Ethernet, USB or TTL port. Additionally, as depicted in the exemplary embodiment shown in FIGS. 1A through 1C, the vital signs measurement apparatus 100 may also include a well 106 for holding a thermometer, and a connector 114 for a pulse oximetry connection.

Figure 2:
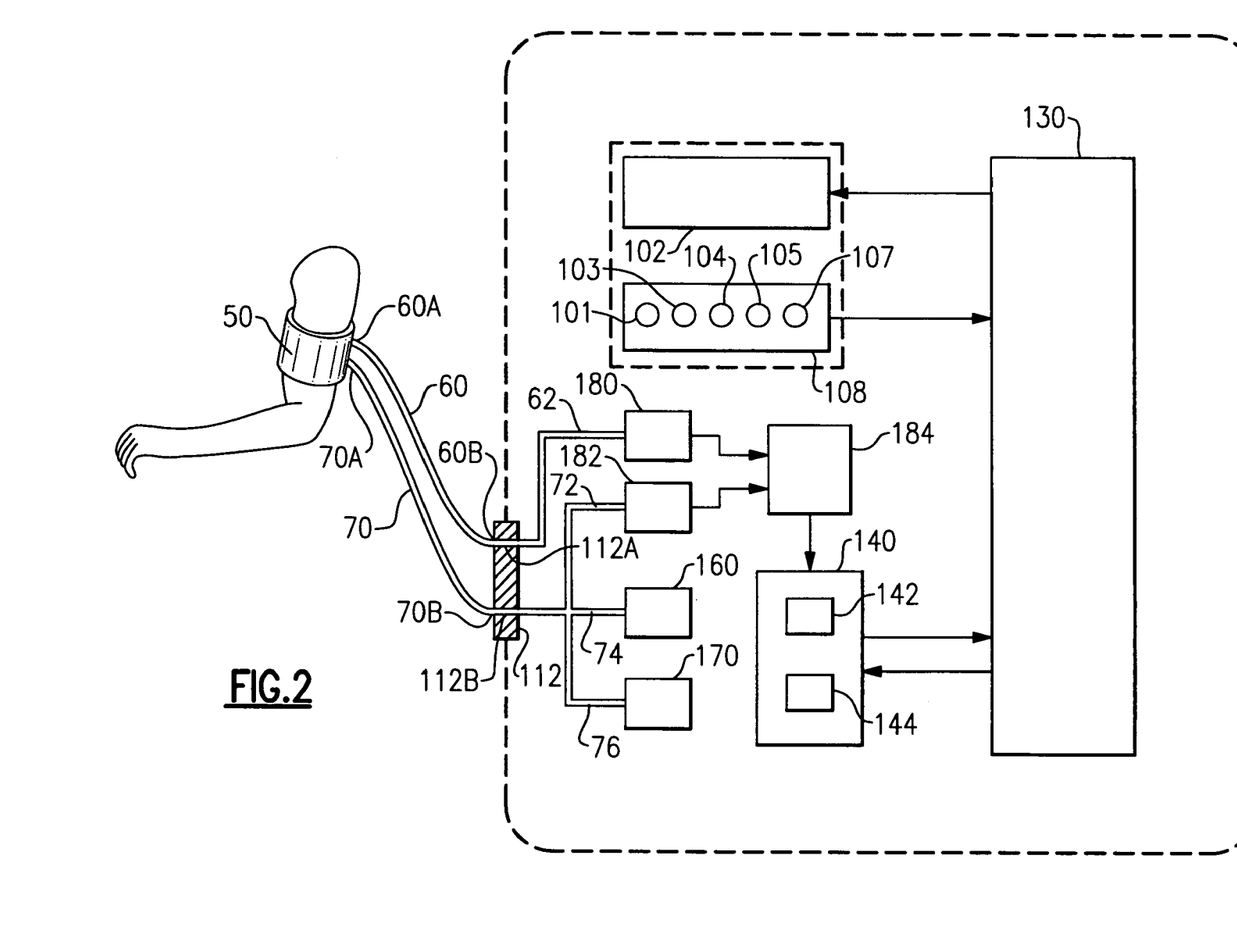
FIG. 2 is a schematic overview illustrating a first embodiment of a system useful in making blood pressure measurements on a non-neonate patient according to the teachings of the invention.
Figures 3, 4:
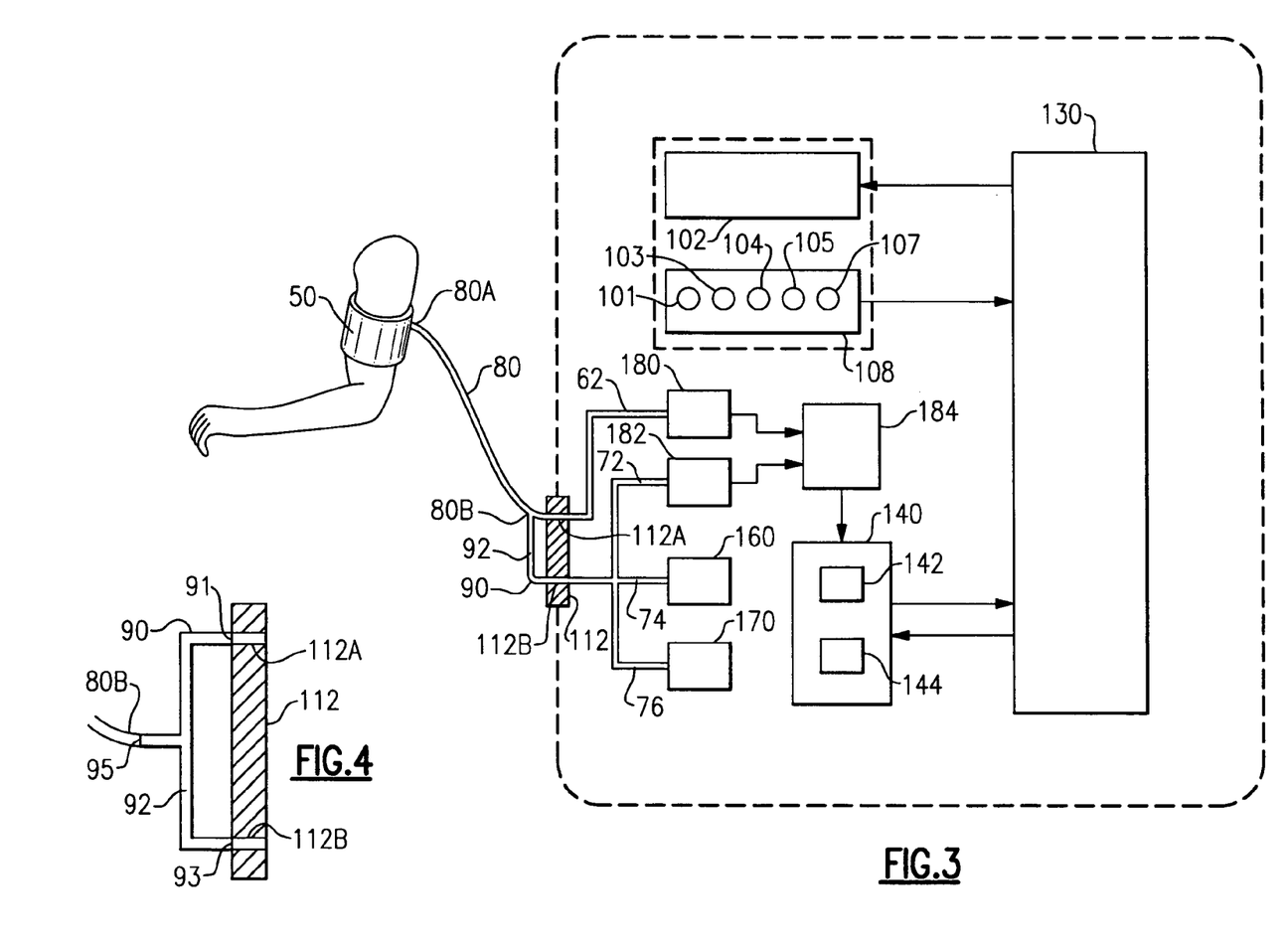
FIG. 3 is a schematic overview illustrating a second embodiment of a system useful in making blood pressure measurements on a neonate patient according to the teachings of the invention.
FIG. 4 is a sectioned plan view of another embodiment of the shunt shown in FIG. 3.

Referring now to FIGS. 2 and 3, the vital signs measurement apparatus 100 includes a microprocessor 130 which interacts with a user interface that includes the display 102 and input keys 101, 103, 104, 105 and 107. The display 102 maybe a LCD display as illustrated in the embodiment shown in the drawings, however, the display 102 may alternatively comprise a touch screen display. If the display 102 is a LCD display, communication is one-way as indicated in FIGS. 2 and 3. If the display 102 is a touch screen display, communication will be bi-directional. The microprocessor 130 also interfaces with the communications ports 120, 122 and 124 to provide capability for communicating bi-directionally with an external device, such as a personal computer or network computer. In a preferred embodiment, the microcontroller 130 is a Motorola DragonBall™ MXL microcontroller available from Motorola, Inc. of Schaumburg, Ill. Other microcontrollers, such as those manufactured by Intel or other semiconductor manufactures, can be substituted for the DragonBall™ MXL microcontroller.

A more detailed description of the portable vital signs measurement apparatus 100 is presented in the aforementioned co-pending U.S. patent application Ser. No. 11/032, 625, filed Jan. 10, 2005, entitled "A Portable Vital Signs Measurement Instrument and Method of Use Thereof".

The vital signs measurement apparatus 100 further includes a pump 160, a valve 170, a NIBP module 140, and a first pressure sensor 180 which operate in association with a blood pressure cuff 50 applied to a limb of a patient to provide for the non-invasive measurement of the systolic and diastolic blood pressures, of the patient. The NIBP module 140 controls operation of the pump 160 and the valve 170. The pump 160, which may be a positive displacement pump or other type of inflation pump, is pneumatically coupled to the blood pressure cuff through a conduit, termed a lumen, and is operable to inflate blood pressure cuff 50 in response to a command signal from the NIBP module 140. The valve 170 is also pneumatically coupled to the blood pressure cuff 50 by a lumen and provides for selective venting of air from the cuff 50 to deflate the cuff under the control of the NIBP module 140. Pump 160 and valve 170 are pneumatically coupled to the cuff 50 through the same lumen via port 112B of the connector 112 of the apparatus 100. Within the apparatus 100, pump 160 and valve 170 communicate pneumatically with port 112B. Additionally, the first pressure sensor 180 communicates pneumatically with port 112A of connector 112 and a second pressure sensor communicates pneumatically with port 112B of the connector 112. The first and second pressure sensors may be conventional pressure transducers or other types of pressure sensing devices. A sensor electronics module 184 is associated with the first and second pressure sensors 180 and 182 for receiving the sensed pressure readings from the pressure sensors, converting those readings to electrical signals indicative of the sensed pressure, and transmitting that digital signal indicative of the sensed pressure to the NIBP module 140.

Once the cuff has been inflated to a pre-selected pressure for the particular cuff in use, the NIBP module 140 will shut the pump 160 off and open the valve 170 to deflate the cuff at a desired rate to enable the patient's diastolic and systolic blood pressures and pulse rate to be measured automatically in a conventional manner as the cuff deflates. The inflation and deflation rate and timing of the cuff 50 are controlled by the NIBP module 140. A more detailed discussion and description of the operation of NIBP module 140 for blood pressure measurement is presented in the aforementioned co-pending U.S. patent application Ser. No. 10/619,380, filed Jul. 14, 2003, entitled "Motion Measurement in a Blood Pressure Measurement Device." It is to be understood, however, that various techniques and procedures accepted in general practice may be employed to automatically measure the patient's systolic and diastolic blood pressures and pulse rate as the cuff deflates.

Referring now to FIG. 2 in particular, a non-neonate cuff 50 is depicted wrapped around a limb of a patient and connected to the connector 112 of the vital signs measurement apparatus 100 for measurement of the blood pressure of the patient. The non-neonate cuff 50 is a two lumen cuff of the type commonly used in connection with electronic monitors when measuring blood pressure in adults, children, and infants of age 29 days and older. Cuffs of this type are available from Welch Allyn, Inc., headquartered in Skaneateles, N.Y., in "monitor" style in sizes for thigh, large adult, adult, small adult, child, small child, and infant. The two lumens 60 and 70 are connected at their respective proximal ends 60A and 70A to the cuff 50 and at their respective distal ends 60B and 70B to the ports 112A and 112B, respectively, of the connector 112. Each lumen 60 and 70 may be a rubber tube or conduit, or a tube or conduit of other suitable material.

Referring now to FIG. 3 in particular, a neonate cuff 50 is depicted wrapped around a limb of a neonate patient and connected to the connector 112 of the vital signs measurement apparatus 100 for measurement of the blood pressure of the patient. The neonate cuff 50 is a single lumen cuff of the type commonly used in connection with electronic monitors when measuring blood pressure in infants of age 28 days and younger. Cuffs of this type are available from Welch Allyn, Inc., headquartered in Skaneateles, N.Y., in "monitor" style sized for neonates. The single lumen 80 is connected at its proximal end 80A directly to the cuff 50 and at its distal end 80B to the port 112A of the connector 112. Additionally, a shunt 90 provides a conduit 92 to additionally connect the single lumen 80 to port 112 B of the connector 112. Lumen 80 may be a rubber tube or conduit, or a tube or conduit of other suitable material. In an embodiment, the shunt 90 may be a rubber tube or conduit, or a tube or conduit of other suitable material, like the lumen 80 and be formed integrally with the single lumen 80 near the distal end 80B thereof. In another embodiment, the shunt 90 may, as illustrated in FIG. 4, comprise a separate component having a body defining a conduit 92 having a first port 91 for connection to port 112A of the connector 112, a second port 93 for connection to port 112B of the connector 112, and third port 95 to which the distal end 80B of the lumen 80 is connected. Each of the ports 91, 93 and 95 opens directly to the conduit 92. Thus, the conduit 92 of the shunt 90 pneumatically communicates the lumen 80 with each of ports 112A and 112B of the connector 112. In either embodiment, the conduit 92 of the shunt 90 is of a relatively short length with respect to the overall length of the lumen 80, that length typically being about 5 feet.

When measuring blood pressure using an automated procedure, it is important that inflation/deflation rates, timing and pressure levels be appropriate for the particular patient whose blood pressure is being measured. In conventional practice, when measuring the blood pressure of a neonate, the maximum pressure to which the cuff is inflated before deflation will be substantially lower than the pressure to which the cuff is inflated when measuring the blood pressure of a non-neonate. Additionally, a step deflation procedure is customarily employed when deflating the measuring the blood pressure of a neonate, while a rapid deflation procedure may be preferred when measuring the blood pressure of a non-neonate.

The pressures measured via the first and second pressure sensors 180 and 182 are monitored during the inflation of the cuff by the NIBP module 140. The pressure readings from the first and second pressure sensors are communicated to the sensor electronics module 184 and converted to electrical signals indicative of the sensed pressures. These pressure signals are communicated to the analysis module 142 of the NIBP module 140. The analysis module 142 is configured to compare the first sensed pressure, represented by the pressure signal derived from the pressure reading from the first pressure sensor 180, to the second sensed pressure signal, represented by the pressure signal derived from the pressure reading from the second pressure sensor, during the inflation period. The analysis module 142 generates a first comparison signal if the first and second sensed pressure signals are not approximately equal to each other, and generates second comparison signal, different from the first pressure signal, if the first and second sensed pressure signals are approximately equal to each other.

Figure 5:
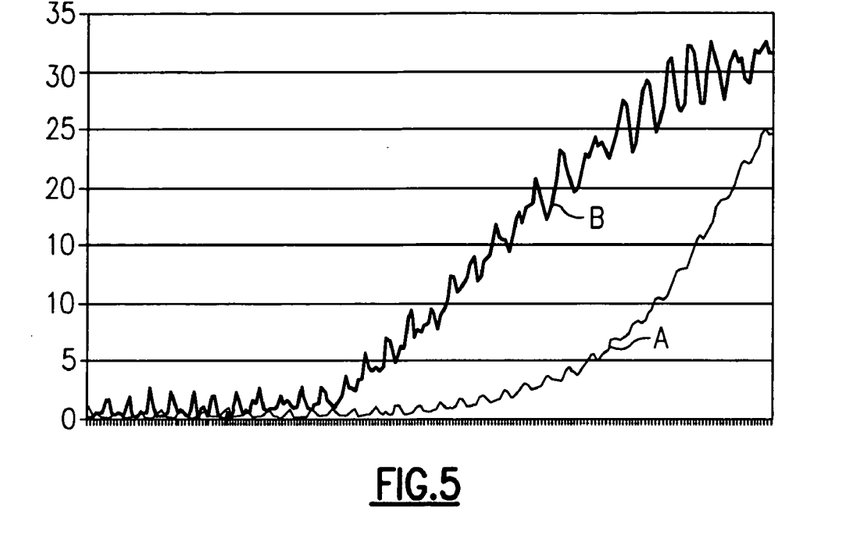
FIG. 5 is a graphical illustration depicting exemplary pressure measurements from the first and second pressure sensors during inflation of a non-neonate cuff.

If a cuff having two lumens is connected to the apparatus 100 as illustrated in FIG. 2, the pressure sensed at the first pressure sensor 180 will significantly lag the pressure sensed at the second pressure sensor 182 as exemplified by the graphical illustration of pressure over time during an exemplary initial inflation period of about two seconds as shown FIG. 5, wherein trace A reflects the pressure at the first pressure sensor 180 and trace B reflects the pressure at the second pressure sensor 182. Typically, the overall time for fully inflate blood pressure cuff 50 via the pump 160 would be about fifteen seconds. The pressure sensed at the first pressure sensor 180 lags the pressure sensed at the second pressure sensor 182, ergo the pressure sensed by the second pressure sensor 182 significantly exceeds the pressure sensed by the first pressure sensor 180 during this initial inflation period, due primarily to the pressure drop experienced as the inflating fluid from the pump 160 passes through the lumen 70. Due to this pressure drop, during the initial inflation of the cuff, the pressure sensed at the first sensor 180 will at a given time be less than the pressure sensed at the second pressure sensor 182.

Figure 6:
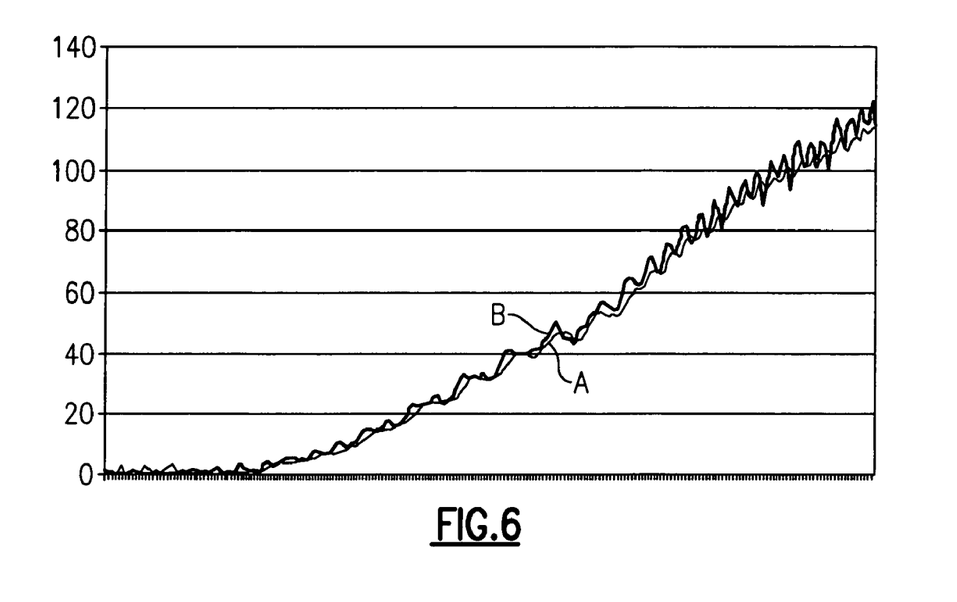
FIG. 6 is a graphical illustration depicting exemplary pressure measurements from the first and second pressure sensors during inflation of a neonate cuff.

However, if a cuff having only a single lumen 80 is connected to the apparatus 110 via a shunt 90 as illustrated in FIG. 3, the pressure sensed at the first pressure sensor 180 will not lag the pressure sensed at the second pressure sensor 182, but rather at any point during the inflation of the cuff, will be approximately equal to the pressure sensed at the second pressure sensor 182 as exemplified by the graphical illustration of pressure over time during an exemplary initial inflation period of about two seconds as shown FIG. 6, wherein trace A reflects the pressure at the first pressure sensor 180 and trace B reflects the pressure at the second pressure sensor 182. Again, the overall time for fully inflate blood pressure cuff 50 via the pump 160 would typically be about fifteen seconds.

In accordance with the invention, this fundamental difference in the relative magnitudes of the respective pressures sensed by the first and second pressure sensors 180, 182 during the inflation of a two lumen cuff versus a single lumen cuff is used by the NIPB module to determine which type of cuff is actually attached to the apparatus 100 whenever a blood pressure measurement procedure is commenced. The NIBP module 140 includes a control module 144 configured to control the operation of the pump 160 in response to receipt of one of either the first comparison signal or the second comparison signal from the analysis module 142. Through the user interface 108 operatively associated with the microprocessor 130, the clinician selects one of either a first blood pressure measurement procedure or a second blood pressure measurement procedure to be conducted by the control module 144. In accord with the invention, the control module 144 will operate to terminate a blood pressure measurement procedure if the pressure comparison signal received from the analysis module 142 does not correspond to the pressure relationship that should be associated with the blood pressure measurement procedure being conducted. For example, an embodiment of the apparatus 100, the clinician may select from a first blood pressure measurement procedure for measurement of the blood pressure of on non-neonate patients only and the second blood pressure measurement procedure for measurement of blood pressure of on neonate patients only. If the non-neonate blood pressure measurement procedure has been selected by the clinician, the NIBP module 140 will initiate inflation of the cuff 50 with the intent of conducting a non-neonate blood pressure measurement procedure. However, if during the cuff inflation period, the control module 144 receives a comparison signal from the analysis module 142 indicating that the respective pressures sensed by the first and second pressure sensors 180 and 182 are approximately equal, the control module will know that a signal lumen neonate cuff has been connected to the apparatus 100 and will automatically terminate the non-neonate blood pressure measurement procedure. This automatic termination of the blood pressure measurement procedure due to the sensed incompatibility of the cuff actually in use with the blood pressure measurement procedure selected by the clinician ensures the safety of a neonate patient by preventing blood pressure measurement using a non-neonate measurement procedure from continuing beyond partial inflation of the cuff 50.

Figure 7:
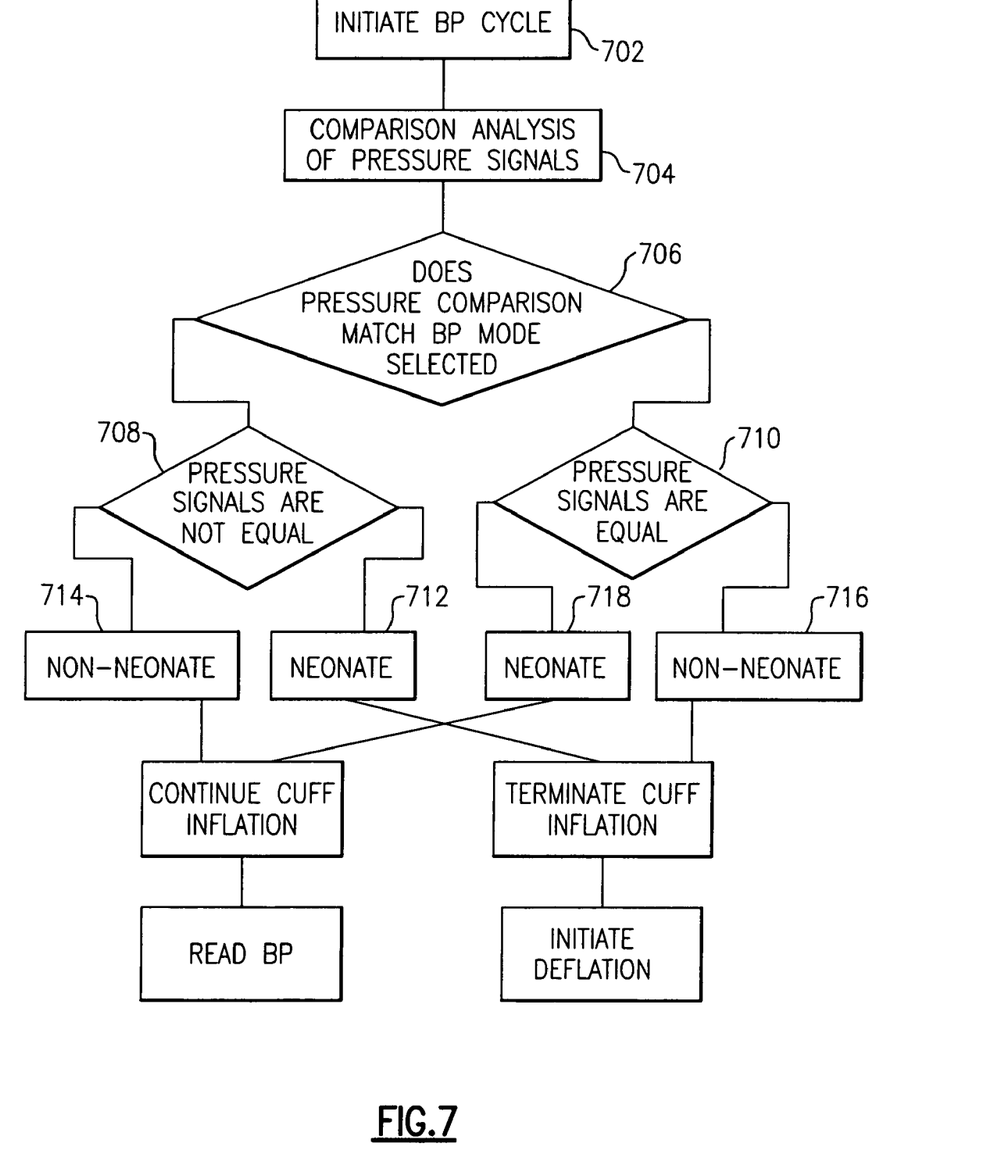
FIG. 7 is a flow chart illustrating a first embodiment of the method of the invention.

An exemplary embodiment of a method of measuring blood pressure providing neonate safety is illustrated by the process flow chart presented in FIG. 7. The chart begins at box 702 labeled "Initiate BP cycle". However, it is to be understood that before initiating the blood pressure process, the clinician connects a blood pressure cuff 50 to the ports 112 A and 112B of the connector 112 of the apparatus 100, turns the apparatus 100 on by depressing the On/Off key 101 of the face of the apparatus 100, and selects the blood pressure mode, i.e. either a non-neonate blood pressure measurement procedure or a neonate blood pressure measurement procedure. To measure the blood pressure of a non-neonate patient, the clinician should connect a two lumen embodiment of cuff 50 to the connector 112 as illustrated in FIG. 2 and also select the non-neonate blood pressure measurement procedure. To measure the blood pressure of a neonate patient, the clinician should connect a single lumen with shunt embodiment of cuff 50 to the connector 112 as illustrated in FIG. 3 and also select the neonate blood pressure measurement procedure. The clinician may connect the blood pressure cuff 50 to the connector 112 either before or after selecting the blood pressure mode to be conducted by the NIBP module 140 of the apparatus 100.

With the cuff 50 connected, the apparatus 100 powered on, and the blood pressure mode selected, as indicated at box 702, the clinician then initiates the selected blood pressure measurement procedure, either neonatal or adult (non-neonatal) mode, by depressing the key 104 on the face of the apparatus 100. As the inflation process begins, the pressure sensors activate and the analysis module 142 of the NIPB module 140 begins, as indicated at box 704, its comparison analysis of the pressure signals received from the sensor electronics module 184 representing the respective pressures sensed by the first and the second pressure sensors 180 and 182 and transmits to the control module 144 either a first pressure comparison signal indicating that the respective pressure sensors are not approximately equal, or a second pressure comparison signal indicating that the respective pressure sensors are approximately equal.

As indicated at box 706, the control module 144 next determines if the pressure relationship indicated by the comparison signal received from the analysis module 142 is compatible with the pressure relationship characteristic of the selected blood pressure mode. If a first comparison signal is received by the control module 144, as indicated by box 708, the control module will terminate inflation of the cuff 50 and abort the blood pressure measurement procedure if the neonate blood pressure mode has been selected, as indicated at box 712, or will continue the inflation of the cuff 50 and proceed with blood pressure measurement if the non-neonate blood pressure mode has been selected, as indicated at box 714. However, if a second comparison signal is received by the control module 144, as indicated by box 710, indicating that the respective pressures sensed by the first and second pressure sensors are approximately equal, the control module will continue inflation of the cuff 50 and proceed with blood pressure measurement if the neonate blood pressure mode has been selected, as indicated at box 716, or will terminate the inflation of the cuff 50 and proceed abort the blood pressure measurement procedure if the non-neonate blood pressure mode has been selected, as indicated at box 718.

Figure 8:
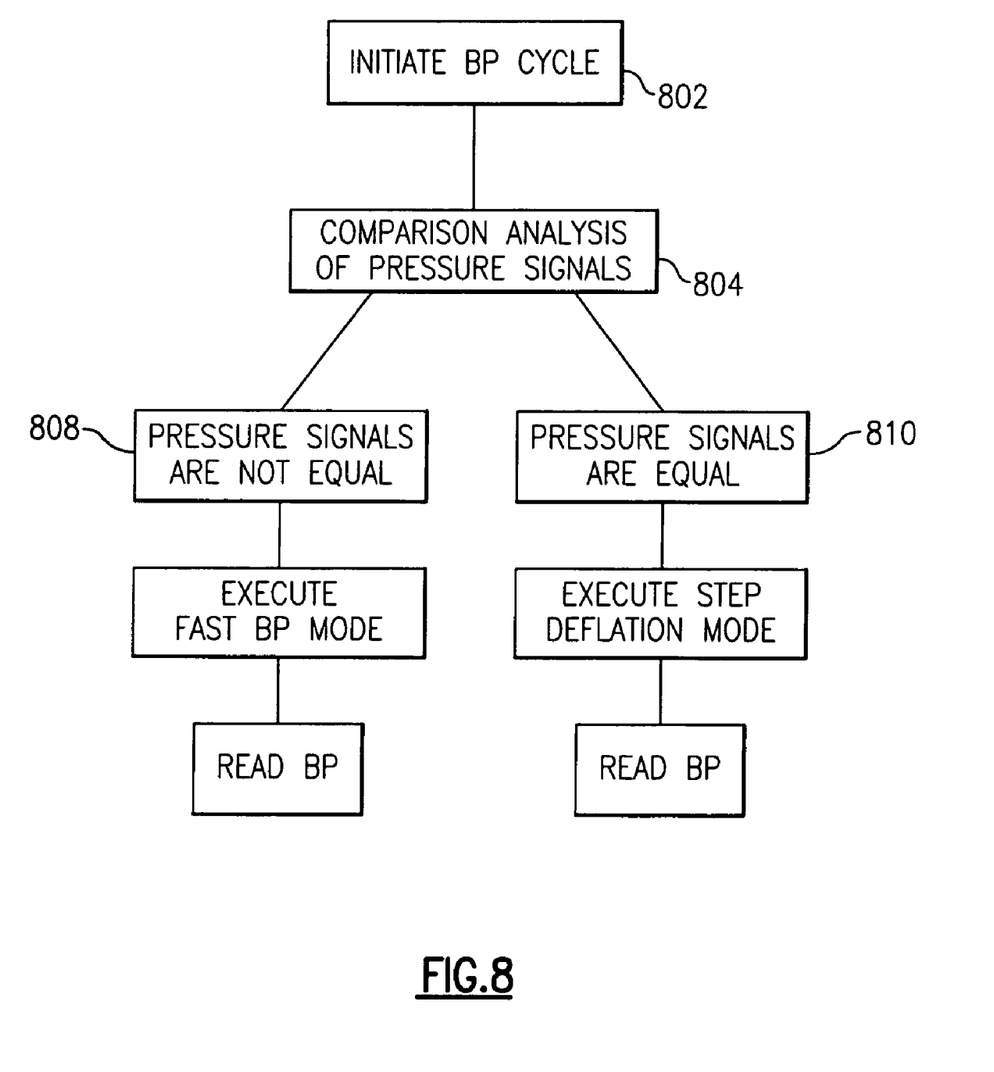
FIG. 8 is a flow chart illustrating a first embodiment of the method of the invention.

An exemplary embodiment of a method of measuring blood pressure providing automatic adjustment of the blood pressure measurement to the cuff installed is illustrated by the process flow chart presented in FIG. 8. The chart begins at box 802 labeled "Initiate BP cycle". However, it is again to be understood that before initiating the blood pressure process, the clinician connects a blood pressure cuff 50 to the ports 112 A and 112B of the connector 112 of the apparatus 100, turns the apparatus 100 on by depressing the On/Off key 101 of the face of the apparatus 100, and selects the blood pressure mode, i.e. either a "Fast Bp mode" blood pressure measurement procedure or a "Step Deflation" blood pressure measurement procedure. To measure the blood pressure of a the patient, the clinician connects either a two lumen embodiment of cuff 50 to the connector 112, as illustrated in FIG. 2, or a single lumen with shunt embodiment of cuff 50 to the connector 112, as illustrated in FIG. 3. The clinician may connect the blood pressure cuff 50 to the connector 112 either before or after selecting the blood pressure mode to be conducted by the NIBP module 140 of the apparatus 100.

With the cuff 50 connected, the apparatus 100 powered on, and the blood pressure mode selected, as indicated at box 802, the clinician then initiates the blood pressure measurement procedure by depressing the key 104 on the face of the apparatus 100. As the inflation process begins, the pressure sensors activate and the analysis module 142 of the NIPB module 140 begins, as indicated at box 804, its comparison analysis of the pressure signals received from the sensor electronics module 184 representing the respective pressures sensed by the first and the second pressure sensors 180 and 182 and transmits to the control module 144 either a first pressure comparison signal indicating that the respective pressure sensors are not approximately equal, or a second pressure comparison signal indicating that the respective pressure sensors are approximately equal.

The control module 144 next determines if the pressure relationship indicated by the comparison signal received from the analysis module 142 is compatible with the pressure relationship characteristic of the selected blood pressure mode. If a first comparison signal is received by the control module 144, as indicated by box 808, the control module will know that a two lumen cuff is attached to the apparatus 100 and will proceed to measure the patient's blood pressure via the "Fast BP", even if the "Step Deflation" mode had been selected. However, if a second comparison signal is received by the control module 144, as indicated by box 810, indicating that the respective pressures sensed by the first and second pressure sensors are approximately equal, the control module will know that a single lumen cuff is attached to the apparatus 100 and proceed with measuring the patient's blood pressure by the "Step Deflation" mode.

In addition to the comparison of pressure signals from pressure sensors 180, 182, the analysis module 142 may also accept and store information such as pump power, whether modulated or stepped, pressure channel noise level, or inflation rise time. The information from these additional inputs combined with the comparison of the pressure signals from pressure sensors 180, 182 may be used to set thresholds that may be used in combination with the aforedescribed pressure monitoring methods for determining the mode of operation in use and for ensuring that the proper blood pressure mode is in use. For example, if the analysis module 142 has determined that the pressure relationships are not sufficient alone for mode determination, the analysis module may refer to the pump power information to gain further insight. A low voltage value for pump power would indicate that a neonate blood pressure measurement procedure is in use, while a high voltage value for pump power would indicate that a non-neonate blood pressure measurement procedure is in use. This additional information in combination with the pressure relationship information would be sufficient for the analysis module to determine whether that mode of operation should be continued.

What is claimed is:

1. A method for blood pressure measurement by means of an inflatable cuff applied to a limb of a vertebrate and pneumatically coupled to a first port and a second port of a blood pressure measurement apparatus having a pump for inflating the cuff pneumatically coupled to the second port, said blood pressure measurement to be conducted via a selected blood pressure measurement procedure, said method comprising the steps of:
   initiating inflation of the inflatable cuff;
   sensing a first pressure through a first pressure sensor pneumatically coupled to the first port;
   sensing a second pressure through a second pressure sensor pneumatically coupled to the second port;
   comparing the magnitude of the first pressure to the magnitude of the second pressure during an initial inflation period to determine a relative relationship between the respective magnitudes of the first pressure and the second pressure; and
   continuing the blood pressure measurement procedure if the relative relationship between the respective magnitudes of the first pressure and the second pressure is characteristic of the selected blood pressure measurement procedure and cuff in use.

2. A method as recited in claim 1, further comprising the step of aborting the blood pressure measurement procedure if the relative relationship between the respective magnitudes of the first pressure and the second pressure is not characteristic of the selected blood pressure measurement procedure.

3. A method as recited in claim 1, further comprising the step of automatically switching to an alternate blood pressure measurement procedure if the relative relationship between the respective magnitudes of the first pressure and the second pressure is not characteristic of the selected blood pressure measurement procedure.

4. A method as recited in claim 1 further comprising the steps of:
   providing a set of options by which to conduct the blood pressure measurement including a first blood pressure measurement procedure associated with a dual lumen cuff configuration and a second blood pressure measurement procedure associated with a single lumen cuff configuration;
   prior to initiating inflation of the inflatable cuff, selecting the first blood pressure measurement procedure from said set of options;
   determining whether the magnitude of the second pressure significantly exceeds the magnitude of the first pressure;
   continuing inflation of the cuff via said selected first blood pressure measurement procedure if the magnitude of the second pressure significantly exceeds the magnitude of the first pressure.

5. A method as recited in claim 4 further comprising the step of terminating inflation of the cuff if the magnitude of the second pressure does not significantly exceed the magnitude of the first pressure.

6. A method as recited in claim 4 further comprising the step of continuing inflation of the cuff via said second blood pressure measurement procedure if the magnitude of the second pressure does not significantly exceed the magnitude of the first pressure.

7. A method for blood pressure measurement by means of an inflatable cuff applied to a limb of a vertebrate and pneumatically coupled to a first port and a second port of a blood pressure measurement apparatus having a pump for inflating the cuff pneumatically coupled to the second port, said method comprising the steps of:
   providing a set of options by which to conduct the blood pressure measurement including a first blood pressure measurement procedure associated with a dual lumen cuff configuration and a second blood pressure measurement procedure associated with a single lumen cuff configuration;
   initiating inflation of the inflatable cuff;
   sensing a first pressure through a first pressure sensor pneumatically coupled to the first port;
   sensing a second pressure through a second pressure sensor pneumatically coupled to the second port;
   comparing the magnitude of the first pressure to the magnitude of the second pressure during an initial inflation period to determine whether the magnitude of the second pressure significantly exceeds the magnitude of the first pressure;
   continuing inflation of the cuff via said first blood pressure measurement procedure if the magnitude of the second pressure significantly exceeds the magnitude of the first pressure; and
   continuing inflation of the cuff via said second blood pressure measurement procedure if the magnitude of the second pressure does not significantly exceed the magnitude of the first pressure.

8. A method as recited in claim 7, wherein the first blood pressure measurement procedure comprises a non-neonate blood pressure measurement procedure and the second blood pressure measurement procedure comprises a neonate blood pressure measurement procedure.

9. A method as recited in claim 7, wherein the first blood pressure measurement procedure comprises measuring the blood pressure during a step deflation of the blood pressure cuff procedure and the second blood pressure measurement procedure comprises measuring the blood pressure during inflation of the cuff.

10. A blood pressure measurement method for protecting a neonate from mistaken application of a non-neonate blood pressure measurement procedure by means of an inflatable cuff applied to a limb of a neonate vertebrate and pneumatically coupled to a first port and a second port of a blood pressure measurement apparatus having a pump for inflating the cuff pneumatically coupled to the second port, said method comprising the steps of:
- initiating inflation of the inflatable cuff;
- sensing a first pressure through a first pressure sensor pneumatically coupled to the first port;
- sensing a second pressure through a second pressure sensor pneumatically coupled to the second port;
- comparing the magnitude of the first pressure to the magnitude of the second pressure;
- determining whether the magnitude of the first pressure and the magnitude of the second pressure are approximately equal;
- continuing inflation of the cuff via said neonate blood pressure measurement procedure if the magnitude of the first pressure is approximately equal to the magnitude of the second pressure; and
- terminating inflation of the cuff if the magnitude of the first pressure is not approximately equal to the magnitude of the second pressure whereby the neonate is protected from mistaken application of a non-neonate blood pressure measurement procedure.

11. As method as recited in claim 10, further comprising the step of deflating the cuff.

12. A blood pressure measurement apparatus for use in connection with an inflatable cuff applied to a limb of a vertebrate, said inflatable cuff being pneumatically coupled to said apparatus by at least one lumen, said apparatus comprising:
- a pump selectively operable to inflate said inflatable cuff during an inflation period, said pump having an outlet pneumatically coupled to said at least one lumen;
- a first pressure sensor operatively associated with said at least one lumen for sensing the pressure in said cuff during an inflation period;
- a second pressure sensor operatively associated with said pump for sensing the pressure in said at least one lumen near the outlet of said pump;
- an analysis module operatively associated with said first pressure sensor for receiving a first sensed pressure signal therefrom and with said second pressure sensor for receiving a second sensed pressure signal therefrom; and
- a control module operatively associated with said pump and said analysis module;
- said analysis module configured to compare the first sensed pressure to the second sensed pressure signal during the inflation period and to generate a first comparison signal if the first and second sensed pressure signals are not approximately equal to each other and to generate a second comparison signal if the first and second sensed pressure signals are approximately equal to each other, and
- said control module configured to control the operation of said pump in response to receipt of one of either the first comparison signal or the second comparison signal from said analysis module to terminate inflation of the cuff in accord with the first blood pressure measurement procedure and proceed with inflation of the cuff in accord with the second blood pressure measurement procedure in the event that said control module receives the second comparison signal from said analysis module, and to terminate inflation of the cuff in accord with the second blood pressure measurement procedure and proceed with inflation of the cuff in accord with the first blood pressure measurement procedure in the event that said control module receives the first comparison signal from said analysis module.

13. A blood pressure measurement apparatus as recited in claim 12 further comprising a user interface operatively associated with said control module, said user interface providing for a user of said apparatus to select one of either a first blood pressure measurement procedure or a second blood pressure measurement procedure to be conducted by said control module.

14. A blood pressure measurement apparatus as recited in claim 12 wherein the first blood pressure measurement procedure is for measurement of the blood pressure on non-neonate vertebrates only.

15. A blood pressure measurement apparatus as recited in claim 12 wherein the second blood pressure measurement procedure is for measurement of the blood pressure on neonate vertebrates only.

16. A blood pressure measurement apparatus as recited in claim 12 wherein the first blood pressure measurement procedure is for measurement of the blood pressure via a dual lumen cuff only.

17. A blood pressure measurement apparatus as recited in claim 12 wherein the second blood pressure measurement procedure is for measurement of the blood pressure via a single lumen cuff only.

18. A blood pressure measurement apparatus for use in connection with an inflatable cuff applied to a limb of a vertebrate, said inflatable cuff being pneumatically coupled to said apparatus by at least one lumen, said apparatus comprising:
- a pump selectively operable to inflate said inflatable cuff during an inflation period, said pump having an outlet pneumatically coupled to said at least one lumen;
- a first pressure sensor operatively associated with said at least one lumen for sensing the pressure in said cuff during an inflation period;
- a second pressure sensor operatively associated with said pump for sensing the pressure in said at least one lumen near the outlet of said pump;
- an analysis module operatively associated with said first pressure sensor for receiving a first sensed pressure signal therefrom and with said second pressure sensor for receiving a second sensed pressure signal therefrom;
- a control module operatively associated with said pump and said analysis module; and
- a user interface operatively associated with said control module, said user interface providing for a user of said apparatus to select one of either a non-neonate blood pressure measurement procedure or a neonate blood pressure measurement procedure to be conducted by said control module;
- said analysis module configured to compare the first sensed pressure to the second sensed pressure signal during the inflation period and to generate a first comparison signal if the first and second sensed pressure signals are not approximately equal to each other and to generate a second comparison signal if the first and second sensed pressure signals are approximately equal to each other, and
- said control module configured to control the operation of said pump in response to receipt of one of either the first comparison signal or the second comparison signal from said analysis module and to terminate inflation of the cuff by said pump in accord with the non-neonate blood pressure measurement procedure in the event that said control module receives the second comparison signal from said analysis module.

19. A blood pressure measurement apparatus for use in connection with an inflatable cuff applied to a limb of a vertebrate, said inflatable cuff being pneumatically coupled to said apparatus by at least one lumen, said apparatus comprising:
- a pump selectively operable to inflate said inflatable cuff during an inflation period, said pump having an outlet pneumatically coupled to said at least one lumen;
- a first pressure sensor operatively associated with said at least one lumen for sensing the pressure in said cuff during an inflation period;
- a second pressure sensor operatively associated with said pump for sensing the pressure in said at least one lumen near the outlet of said pump;
- an analysis module operatively associated with said first pressure sensor for receiving a first sensed pressure signal therefrom and with said second pressure sensor for receiving a second sensed pressure signal therefrom;
- a control module operatively associated with said pump and said analysis module; and
- a user interface operatively associated with said control module, said user interface providing for a user of said apparatus to select one of either a non-neonate blood pressure measurement procedure or a neonate blood pressure measurement procedure to be conducted by said control module;
- said analysis module configured to compare the first sensed pressure to the second sensed pressure signal during the inflation period and to generate a first comparison signal if the first and second sensed pressure signals are not approximately equal to each other and to generate a second comparison signal if the first and second sensed pressure signals are approximately equal to each other, and
- said control module configured to control the operation of said pump in response to receipt of one of either the first comparison signal or the second comparison signal from said analysis module and to continue inflation of the cuff by said pump in accord with the non-neonate blood pressure measurement procedure so long as said control module receives the first comparison signal from said analysis module.

20. A blood pressure measurement apparatus for use in connection with an inflatable cuff applied to a limb of a vertebrate, said inflatable cuff being pneumatically coupled to said apparatus by at least one lumen, said apparatus comprising:
- a pump selectively operable to inflate said inflatable cuff during an inflation period, said pump having an outlet pneumatically coupled to said at least one lumen;
- a first pressure sensor operatively associated with said at least one lumen for sensing the pressure in said cuff during an inflation period;
- a second pressure sensor operatively associated with said pump for sensing the pressure in said at least one lumen near the outlet of said pump;
- an analysis module operatively associated with said first pressure sensor for receiving a first sensed pressure signal therefrom and with said second pressure sensor for receiving a second sensed pressure signal therefrom;
- a control module operatively associated with said pump and said analysis module; and
- a user interface operatively associated with said control module, said user interface providing for a user of said apparatus to select one of either a non-neonate blood pressure measurement procedure or a neonate blood pressure measurement procedure to be conducted by said control module;
- said analysis module configured to compare the first sensed pressure to the second sensed pressure signal during the inflation period and to generate a first comparison signal if the first and second sensed pressure signals are not approximately equal to each other and to generate a second comparison signal if the first and second sensed pressure signals are approximately equal to each other, and
- said control module configured to control the operation of said pump in response to receipt of one of either the first comparison signal or the second comparison signal from said analysis module and to terminate inflation of the cuff by said pump in accord with the neonate blood pressure measurement procedure in the event that said control module receives the first comparison signal from said analysis module.

21. A blood pressure measurement apparatus for use in connection with an inflatable cuff applied to a limb of a vertebrate, said inflatable cuff being pneumatically coupled to said apparatus by at least one lumen, said apparatus comprising:
- a pump selectively operable to inflate said inflatable cuff during an inflation period, said pump having an outlet pneumatically coupled to said at least one lumen;
- a first pressure sensor operatively associated with said at least one lumen for sensing the pressure in said cuff during an inflation period;
- a second pressure sensor operatively associated with said pump for sensing the pressure in said at least one lumen near the outlet of said pump;
- an analysis module operatively associated with said first pressure sensor for receiving a first sensed pressure signal therefrom and with said second pressure sensor for receiving a second sensed pressure signal therefrom;
- a control module operatively associated with said pump and said analysis module; and
- a user interface operatively associated with said control module, said user interface providing for a user of said apparatus to select one of either a non-neonate blood pressure measurement procedure or a neonate blood pressure measurement procedure to be conducted by said control module;
- said analysis module configured to compare the first sensed pressure to the second sensed pressure signal during the inflation period and to generate a first comparison signal if the first and second sensed pressure signals are not approximately equal to each other and to generate a second comparison signal if the first and second sensed pressure signals are approximately equal to each other, and
- said control module configured to control the operation of said pump in response to receipt of one of either the first comparison signal or the second comparison signal from said analysis module and to continue inflation of the cuff by said pump in accord with the neonate blood pressure measurement procedure so long as said control module receives the second comparison signal from said analysis module.

* * * * *